United States Patent [19]

Guenther et al.

[11] Patent Number: 5,637,704
[45] Date of Patent: Jun. 10, 1997

[54] PREPARATION OF HYDROXYOXAALKYLMELAMINES

[75] Inventors: Erhard Guenther, Ludwigshafen; Wolfgang Reuther, Heidelberg; Günter Scherr, Ludwigshafen; Manfred Dimmler, Dannstadt-Schauernheim, all of Germany

[73] Assignee: BASF Aktiengesellschaft, Ludwigshafen, Germany

[21] Appl. No.: 645,046

[22] Filed: May 13, 1996

Related U.S. Application Data

[63] Continuation of Ser. No. 303,486, Sep. 9, 1994.

[30] Foreign Application Priority Data

Sep. 15, 1993 [DE] Germany .................. 43 31 233.0

[51] Int. Cl.⁶ .................................................. C07D 251/54
[52] U.S. Cl. ...................... 544/196; 544/194; 544/200
[58] Field of Search ............................. 544/194, 196, 544/200

[56] References Cited

U.S. PATENT DOCUMENTS

| | | | |
|---|---|---|---|
| 4,618,676 | 10/1986 | Ebel et al. | 544/196 |
| 4,668,785 | 5/1987 | Ebel et al. | 544/196 |
| 4,670,558 | 6/1987 | Ebel et al. | 544/196 |
| 4,886,882 | 12/1989 | Ebel et al. | 544/196 |
| 5,084,488 | 1/1992 | Weiser et al. | 521/187 |

FOREIGN PATENT DOCUMENTS

| | | |
|---|---|---|
| 0051753 | 5/1982 | European Pat. Off. . |
| 225433 | 6/1987 | European Pat. Off. . |
| 408947 | 1/1991 | European Pat. Off. . |

*Primary Examiner*—Yogendra N. Gupta
*Attorney, Agent, or Firm*—Keil & Weinkauf

[57] ABSTRACT

A process for the preparation hydroxyoxaalkylmelamines of the general formula I

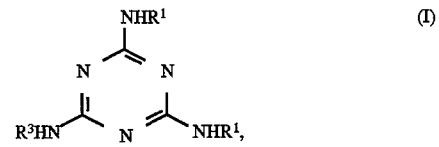

in which $R^1$ denotes a residue of the general formula II

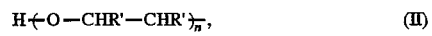

in which the radicals R' can be the same or different and stand for hydrogen or $C_1$–$C_4$ alkyl and $\underline{n}$ denotes 2 or 3 and the radicals $R^2$ and $R^3$ stand for one of the radicals $R^1$ or hydrogen, by the reaction of melamine with a compound of the general formula III

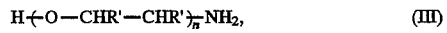

in which R' and $\underline{n}$ have the meanings stated above, at a temperature of from 120° to 250° C. and in the presence of an acid catalyst, in which the acid catalyst is used in a concentration of from 0.01 to 0.15 mol and preferably from 0.02 to 0.12 mol and more preferably from 0.03 to 0.1 mol, based on 1 mol of melamine.

2 Claims, No Drawings

PREPARATION OF HYDROXYOXAALKYLMELAMINES

This application is a continuation of application Ser. No. 08/303,486, filed on Sep. 9, 1994.

The invention relates to an improved process for the preparation of hydroxyoxaalkylmelamines.

Hydroxyoxaalkylmelamines are valuable intermediates for the preparation of urethanes and are also highly suitable for modifying aminoplast resins (cf EP-A 408,947).

EP-A 225,433 describes a process for the preparation of hydroxyoxaalkylmelamines of the formula I

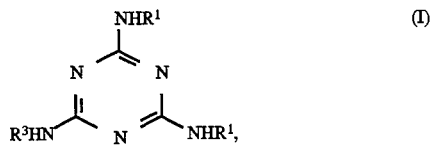

in which $R^1$ denotes a residue of the formula II

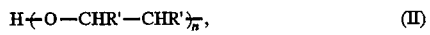

in which the radicals R' can be the same or different and stand for hydrogen or $C_1$–$C_4$ alkyl and $\underline{n}$ denotes 2 or 3 and the radicals $R^2$ and $R^3$ stand for one of the radicals $R^1$ or hydrogen, by the reaction of melamine with a compound of the formula III

in which R' and $\underline{n}$ have the meanings stated above, at a temperature of 120° to 120° C. and in the presence of an acid catalyst.

The acid catalyst is used in an amount of from 0.05 to 3 mol and preferably from 0.1 to 1 mol, based on 1 mol of melamine. As the amount of catalyst increases an increase in the reaction rate is observable.

Suitable acid catalysts are, as revealed in EP-A 225,433, all strong and medium-strength proton acids, for example, hydrofluoric acid, hydrochloric acid, hydrobromic acid, sulfuric acid, nitric acid, phosphoric acid, amidosulfonic acid, thiocyanic acid, p-toluenesulfonic acid, or methanesulfonic acid and Lewis acids, such as boron trifluoride, aluminum chloride, tin(IV) chloride, antimony(V) fluoride, or iron(III) bromide.

Thus it is an object of the present invention to effect further improvement of this prior process with regard to a reduction of the overall time required for production. At the same time, it is desirable to attain an improved product quality.

Surprisingly, this object is achieved by the use of a process for the preparation of hydroxyoxaalkylmelamines of the formula I

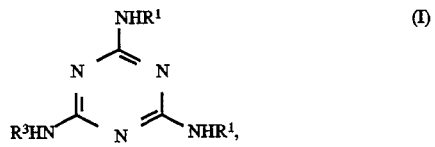

in which $R^1$ denotes a residue of the general formula II

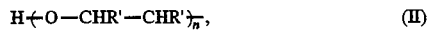

in which the radicals R' can be the same or different and stand for hydrogen or $C_1$–$C_4$ alkyl and $\underline{n}$ denotes 2 or 3 and the radicals $R^2$ and $R^3$ stand for one of the radicals $R^1$ or hydrogen, by the reaction of melamine with a compound of the formula III

in which R' and $\underline{n}$ have the meanings stated above, at a temperature of from 120° to 250° C. and in the presence of an acid catalyst, wherein the acid catalyst is used in a concentration of from 0.01 to 0.15 mol and preferably from 0.02 to 0.12 mol and more preferably from 0.03 to 0.1 mol, based on 1 mol of melamine.

The acid catalysts used can be the aforementioned catalysts. Preferably however ammonium chloride and/or hypophosphorous acid are used ($H_3PO_2$).

In the process of the invention, it is preferred to prepare hydroxyoxaalkylmelamines of the formula I in which R' stands for hydrogen and $\underline{n}$ denotes 2.

These are the compounds N-mono-(5-hydroxy-3-oxapentyl)melamine, N,N'-bis(5-hydroxy-3-oxapentyl)melamine, N,N',N''-tris-(5-hydroxy-3-oxapentyl)melamine, and mixtures thereof.

The oxaalkanolamines of the formula III used as starting compounds are known in the art or can be prepared by conventional methods, cf M. S. Malinskii, A. N. Korchagina, A. G. Yudasina, D. G. Yurko Vorpr. *Khim. Khim. Teknol.* 1974, 34, 6–11 (Russia) and JP-A 79–3005.

The process is generally carried out by placing a mixture of melamine, oxaalkanolamine (e.g. 2,2'-aminoethoxyethanol), an acid catalyst and, optionally, a solvent in a reactor and heating it, with stirring, at a temperature of from 120° to 250° and preferably from 150° to 230° C.

It is general to operate at atmospheric pressure. For the upper temperature range (from 230° to 250° C.), however, a pressure of from 1 to 15 bar must usually be maintained.

Furthermore, it is advisable to carry out the reaction in the presence of a protective gas. The protective gas is generally passed over the surface of the reaction mixture. Examples of suitable protective gases are noble gases and, in particular, nitrogen.

The process of the invention is preferably carried out in the absence of solvents, but it is also possible to carry out the process using an organic solvent. In particular, polyols are suitable for this purpose, for example, ethylene glycol, 1,2-propylene glycol, diethylene glycol, or triethylene glycol.

The amount of oxaalkanolamine used (for example, 2,2'-aminoethoxyethanol) is arbitrary. However, it is preferred to use an excess of amine. Usually from 3 to 10 mol of amine are used per mol of melamine.

The reaction can be monitored using analytical procedures, for example, by means of high-pressure liquid chromatography (HPLC). The reaction can be stopped at any desired degree of conversion, to give, for example, mixtures of N,N',N''-tris(5-hydroxy-3-oxapentyl)melamine, N,N'-bis(5-hydroxy-3-oxapentyl)melamine and, optionally, N-mono (5-hydroxy-3-oxapentyl)melamine, which have a specific reproducibly composition.

At quantitative conversion, pure N,N',N''-tris(5-hydroxy-3-oxapentyl)melamine is obtained.

To effect isolation of the desired product the respective catalyst acid is advantageously neutralized by adding a base, for example, sodium hydroxide, potassium hydroxide, sodium carbonate, potassium carbonate, calcium carbonate, or barium carbonate, to the reaction mixture.

A further advantage of the process of the invention is that the removal of the resulting salts by filtration can be omitted.

In large-scale production filtration causes considerable process engineering costs, since, for example, the salts formed during neutralization are produced in a very fine crystalline form in aminoethoxyethanol acting as solvent and entail long filtering times and thus long production times.

Moreover, when the acid catalyst is used in the form of an ammonium compound, said filtration must take place in an encased filtering unit on account of the unpleasant odor caused by dissolved ammonia, or the ammonia must be removed prior to filtration by applying a vacuum, which likewise causes longer production times.

Furthermore, in order to achieve a sufficiently low viscosity of the filtered solution, the oxaalkanolamine must be used in great excess over the melamine. This causes a relatively low output per unit volume of the reactor.

In the process of the invention, however, it is possible to use a quantity of melamine which is distinctly greater than that of oxaalkanolamine (for example, from 3 to 5 mol of oxaalkanolamine per mole of melamine). This leads to a significant increase in output per unit volume of reactor.

Following neutralization, the excess oxaalkanolamine can be removed by distillation, for example, under reduced pressure (ca 10 mbar) at a temperature of ca 190° C., during which process the almost colorless residue solidifies to form a resin.

We have found that, surprisingly, the hydroxyoxaalkylmelamines prepared by the process of the invention are distinctly lighter in color (color number from 10 to 30) than when prepared by conventional processes (color number from 80 to 150). This is all the more so when hypophosphorous acid is used alone or in conjunction with other acids (color number 0 to 1).

In addition, the process of the invention facilitates parameter setting to achieve a given composition of the product. Due to the absence of a filtration step, in particular, the total time required for production decreases by ca 25%.

In the following examples the percentages are by weight.

EXAMPLES

Example 1

To a mixture of 135 g (1.07 mol) of melamine and 450 g (4.29 mol) of 2,2'-aminoethoxyethanol ("aminodiglycol") there were added, with stirring, 5.3 g (0.1 mol) of ammonium chloride. The mixture was then stirred whilst flushing with a weak stream of nitrogen until the desired composition was achieved (mono:bis:tris-(5-hydroxy-3-oxapentyl) melamine=10:50:40 mol %, HPLC control) at 195° C. Following cooling to 90° C. the mixture was neutralized with 7.95 g of caustic soda solution (50% strength). The removal of the excess amine by distillation in vacuo yielded 352 g of a pale yellow resin (color number: 15; pH=10.7).

Example 2

To a mixture of 630 g (5.00 mol) of melamine and 1575 g (15 mol) of 2,2'-aminoethoxyethanol there were added, with stirring, 5.0 g (30 mmol) of hypophosphorous acid (50% in water) as well as 9.25 g (173 mmol) of ammonium chloride. The mixture was stirred whilst flushing with a weak stream of nitrogen until the desired composition was achieved (mono:bis:tris-(5-hydroxy-3-oxapentyl) melamine=10:50:40 mol %, HPLC control) at 195° C. The excess amine was then removed by distillation in vacuo. Following cooling to 90° C. the mixture was neutralized with 16 g of caustic soda solution (50% strength). 2405 g of a colorless resin were obtained (color number 0 to 1; pH=10.8).

Example 3

To a mixture of 630 g (5.00 mol) of melamine and 1575 g (15 mol) of 2,2'-aminoethoxyethanol there were added, with stirring, 5.0 g (30 mmol) of hypophosphorous acid (50% in water) as well as 20 g (173 mmol) of phosphoric acid (85% in water).

The mixture was then stirred whilst flushing with a weak stream of nitrogen until the desired composition was achieved (mono:bis:tris-(5-hydroxy-3-oxapentyl) melamine=10:50:40 mol %, HPLC control) at 195° C. The excess amine was then removed by distillation in vacuo and neutralized, following cooling to 90° C., with 50 g of caustic soda solution (50% strength). There were obtained 2410 g of a colorless resin (color number 0 to 1; pH=11.0).

We claim:

1. A process for the preparation of hydroxyoxaalkylmelamines having a color number in the range of 0 to 1 of the formula I

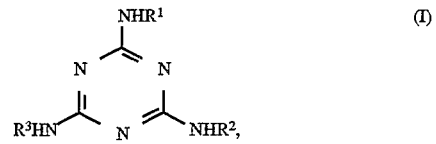

in which the $R^1$ denotes a residue of the general formula II

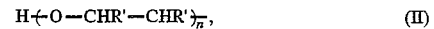

in which the radicals $R^1$ can be the same or different and stand for hydrogen or $C_1$-$C_4$-alkyl and $n$ denotes 2 or 3 and the radicals $R^2$ and $R^3$ stand for one of the radicals $R^1$ or hydrogen, which process comprises: reacting melamine with a compound of the formula III

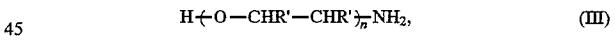

in which R' and $n$ have the meanings stated above, at a temperature of from 120° to 250° C. and in the presence of phosphonic acid as an acid catalyst, the acid catalyst being used in a concentration of from 0.01 to 0.15 mol, based on 1 mol of melamine; wherein phosphonic acid is used in conjunction with a strong or a medium strength proton acid; said process being conducted in the absence of a filtration step.

2. The process of claim 1, wherein the strong or medium strength proton acid which is used with phosphonic acid is selected from the group consisting of hydrofluoric, hydrochloric, hydrobromic, sulfuric, nitric, phosphoric, amidosulfonic, thiocyanic, p-toluenesulfonic and methanesulfonic acid and Lewis acids.

* * * * *